(12) United States Patent
Kirschman

(10) Patent No.: US 8,262,697 B2
(45) Date of Patent: Sep. 11, 2012

(54) MODULAR INTERSPINOUS FIXATION SYSTEM AND METHOD

(75) Inventor: David Louis Kirschman, Dayton, OH (US)

(73) Assignee: X-spine Systems, Inc., Miamisburg, OH (US)

( * ) Notice: Subject to any disclaimer, the term of this patent is extended or adjusted under 35 U.S.C. 154(b) by 228 days.

(21) Appl. No.: 12/687,168

(22) Filed: Jan. 14, 2010

(65) Prior Publication Data
US 2011/0172711 A1    Jul. 14, 2011

(51) Int. Cl.
*A61B 17/70* (2006.01)

(52) U.S. Cl. .......... 606/248; 606/249

(58) Field of Classification Search .......... 606/246–249; 623/17.11–17.16
See application file for complete search history.

(56) References Cited

U.S. PATENT DOCUMENTS

| | | |
|---|---|---|
| 2,677,369 A | 5/1954 | Knowles |
| 3,426,364 A | 2/1969 | Lumb |
| 3,648,691 A | 3/1972 | Lumb et al. |
| 4,257,409 A | 3/1981 | Bacal et al. |
| 4,401,112 A | 8/1983 | Rezaian |
| 4,604,995 A | 8/1986 | Stephens et al. |
| 4,611,582 A | 9/1986 | Duff |
| 4,657,550 A | 4/1987 | Daher |
| 4,696,290 A | 9/1987 | Steffee |
| 4,790,303 A | 12/1988 | Steffee |
| 4,827,918 A | 5/1989 | Olerud |
| 5,180,381 A | 1/1993 | Aust et al. |
| 5,366,455 A | 11/1994 | Dove et al. |
| 5,454,812 A | 10/1995 | Lin |
| 5,496,318 A | 3/1996 | Howland et al. |
| 5,609,636 A | 3/1997 | Kohrs et al. |
| 5,645,599 A | 7/1997 | Samani |
| 5,672,175 A | 9/1997 | Martin |
| 5,702,452 A | 12/1997 | Argenson et al. |
| 5,702,453 A | 12/1997 | Rabbe et al. |
| 5,800,548 A | 9/1998 | Martin et al. |
| 5,836,948 A | 11/1998 | Zucherman et al. |
| 5,860,977 A | 1/1999 | Zucherman et al. |
| 5,876,404 A | 3/1999 | Zucherman et al. |
| 6,048,342 A | 4/2000 | Zucherman et al. |
| 6,068,630 A | 5/2000 | Zucherman et al. |
| 6,090,112 A | 7/2000 | Zucherman et al. |
| 6,132,464 A | 10/2000 | Martin |

(Continued)

FOREIGN PATENT DOCUMENTS
WO    2008052071 A2    5/2008

*Primary Examiner* — Eduardo C Robert
*Assistant Examiner* — Christina Negrelli
(74) *Attorney, Agent, or Firm* — Jacox, Meckstroth & Jenkins (57) ABSTRACT

A modular interspinous fixation system and method are shown. The system and method comprise a first plate, a second plate and a locking cross bar for locking the first and second plates together and into locked engagement with a first spinous process and a second spinous process. A bridge is mounted or received on the locking cross bar so that it becomes locked onto the locking cross bar when the locking cross bar is in locked engagement. The bridge and locking cross bar are adapted so that the bridge does not rotate about its axis while on the locking cross bar. Various other embodiments are shown illustrating various bridges of different shapes and sizes, integral and non-integral locking cross bars and even a ramped locking cross bar for facilitating preventing separation of the first and second plates after they are mounted to the first and second spinous processes.

91 Claims, 7 Drawing Sheets

U.S. PATENT DOCUMENTS

| | | |
|---|---|---|
| 6,152,926 A | 11/2000 | Zucherman et al. |
| 6,156,038 A | 12/2000 | Zucherman et al. |
| 6,183,471 B1 | 2/2001 | Zucherman et al. |
| 6,190,387 B1 | 2/2001 | Zucherman et al. |
| 6,235,030 B1 | 5/2001 | Zucherman et al. |
| 6,238,397 B1 | 5/2001 | Zucherman et al. |
| 6,332,882 B1 | 12/2001 | Zucherman et al. |
| 6,332,883 B1 | 12/2001 | Zucherman et al. |
| 6,358,254 B1 | 3/2002 | Anderson |
| 6,364,883 B1 | 4/2002 | Santilli |
| 6,379,355 B1 | 4/2002 | Zucherman et al. |
| 6,419,676 B1 | 7/2002 | Zucherman et al. |
| 6,419,677 B2 | 7/2002 | Zucherman et al. |
| 6,440,169 B1 | 8/2002 | Elberg et al. |
| 6,451,019 B1 | 9/2002 | Zucherman et al. |
| 6,451,020 B1 | 9/2002 | Zucherman et al. |
| 6,478,796 B2 | 11/2002 | Zucherman et al. |
| 6,500,178 B2 | 12/2002 | Zucherman et al. |
| 6,514,256 B2 | 2/2003 | Zucherman et al. |
| 6,579,319 B2 | 6/2003 | Goble et al. |
| 6,582,433 B2 | 6/2003 | Yun |
| 6,626,944 B1 | 9/2003 | Taylor |
| 6,641,585 B2 | 11/2003 | Sato et al. |
| 6,652,527 B2 | 11/2003 | Zucherman et al. |
| 6,652,534 B2 | 11/2003 | Zucherman et al. |
| 6,695,842 B2 | 2/2004 | Zucherman et al. |
| 6,699,246 B2 | 3/2004 | Zucherman et al. |
| 6,699,247 B2 | 3/2004 | Zucherman et al. |
| 6,712,819 B2 | 3/2004 | Zucherman et al. |
| 6,761,720 B1 | 7/2004 | Senegas |
| 6,946,000 B2 | 9/2005 | Senegas et al. |
| 6,964,883 B2 | 11/2005 | Chang |
| 7,029,473 B2 | 4/2006 | Zucherman et al. |
| 7,048,736 B2 | 5/2006 | Robinson et al. |
| 7,087,083 B2 | 8/2006 | Pasquet et al. |
| 7,201,751 B2 | 4/2007 | Zucherman et al. |
| 7,306,628 B2 | 12/2007 | Zucherman et al. |
| 7,335,203 B2 | 2/2008 | Winslow et al. |
| 7,510,567 B2 | 3/2009 | Zucherman et al. |
| 7,549,999 B2 | 6/2009 | Zucherman et al. |
| 7,585,313 B2 | 9/2009 | Kwak et al. |
| 7,585,316 B2 | 9/2009 | Trieu |
| 7,588,591 B2 | 9/2009 | Hartmann et al. |
| 7,588,592 B2 | 9/2009 | Winslow et al. |
| 7,621,939 B2 | 11/2009 | Zucherman et al. |
| 7,628,816 B2 | 12/2009 | Magerl et al. |
| 7,635,377 B2 | 12/2009 | Zucherman et al. |
| 7,658,752 B2 | 2/2010 | Labrom et al. |
| 7,666,208 B1 | 2/2010 | Asfora |
| 7,670,380 B2 | 3/2010 | Cauthen, III |
| 7,691,130 B2 | 4/2010 | Bruneau et al. |
| 7,695,496 B2 | 4/2010 | Labrom et al. |
| 7,727,233 B2 | 6/2010 | Blackwell et al. |
| 7,763,073 B2 | 7/2010 | Hawkins et al. |
| 2002/0029039 A1 | 3/2002 | Zucherman et al. |
| 2002/0065557 A1 | 5/2002 | Goble et al. |
| 2002/0091446 A1 | 7/2002 | Zucherman et al. |
| 2002/0143331 A1 | 10/2002 | Zucherman et al. |
| 2003/0040746 A1 | 2/2003 | Mitchell et al. |
| 2003/0139812 A1 | 7/2003 | Garcia et al. |
| 2005/0203512 A1 | 9/2005 | Hawkins et al. |
| 2005/0240182 A1 | 10/2005 | Zucherman et al. |
| 2006/0004447 A1 | 1/2006 | Mastrorio et al. |
| 2006/0015181 A1 | 1/2006 | Elberg |
| 2006/0064166 A1 | 3/2006 | Zucherman et al. |
| 2006/0106381 A1 | 5/2006 | Ferree et al. |
| 2006/0142761 A1 | 6/2006 | Landry et al. |
| 2006/0235533 A1 | 10/2006 | Blain |
| 2006/0247634 A1 | 11/2006 | Warner et al. |
| 2006/0247640 A1 | 11/2006 | Blackwell et al. |
| 2006/0264938 A1 | 11/2006 | Zucherman et al. |
| 2006/0282079 A1 | 12/2006 | Labrom et al. |
| 2007/0055246 A1 | 3/2007 | Zucherman et al. |
| 2007/0233082 A1 | 10/2007 | Chin et al. |
| 2007/0270840 A1 | 11/2007 | Chin et al. |
| 2008/0177306 A1 | 7/2008 | Lamborne et al. |
| 2008/0177391 A1* | 7/2008 | Mitchell et al. ............ 623/17.16 |
| 2008/0183210 A1 | 7/2008 | Zucherman et al. |
| 2008/0183211 A1 | 7/2008 | Lamborne et al. |
| 2010/0211101 A1 | 8/2010 | Blackwell et al. |
| 2011/0066186 A1 | 3/2011 | Boyer, II et al. |

* cited by examiner

MODULAR INTERSPINOUS FIXATION SYSTEM AND METHOD

BACKGROUND OF THE INVENTION

1. Field of the Invention

This invention relates to fixation systems and, more particularly, to a modular interspinous fixation system including a modular bridge or sleeve member that can be received on a locking cross bar so that at least of a portion of the bridge and locking cross bar can be received in at least one of the plates and locked therein when the first and second plates are mounted together. The bridge and locking cross bar are adapted to prevent relative rotation.

2. Description of the Related Art

Many types of devices for a surgical stabilization of a spine have been developed. Various screw, rod and plating implants have been utilized for the purpose of stabilizing the spine for the purposes of fixation and spinal fusion. Until recently, such devices have been large constructs requiring extensive surgical exposure and operative time. There is an ongoing shift to providing spinal stabilization for fusion using more compact devices. Furthermore, there is an increased need to be able to tailor these devices to the individual anatomy of a specific patient or the treatments needs of an individual disease process.

Several inventors have utilized the anatomy of the spinous process, the bony protrusion on the posterior portion of the vertebra, as a fixation point for device placement. Various early implants designed for fixation onto the spinous process include U.S. Pat. Nos. 3,426,364; 4,257,409; 4,604,995; 4,696,290; and 34,827,918, all of which are incorporated herein by reference and made a part hereof.

More recently, devices which affix to the spinous processes of adjacent vertebrae have been developed, including U.S. Pat. Nos. 5,645,599; 5,836,948; 5,860,977; 6,048,342; 6,068,630; 6,440,169; 6,451,019; 6,478,796; 6,582,433; 6,641,585; 6,964,883; 6,695,842; 7,048,736; 7,201,751; 7,306,628; 7,585,316; and U.S. Patent Publication Nos. 32008/0177306 and 32008/0183211, all of which are incorporated herein by reference and made a part hereof. The prior art, however does not fully address the needs, so what is needed is a system and method that improves upon the prior art.

SUMMARY OF THE INVENTION

An object of one embodiment is to provide a modular interspinous fixation system and method that utilizes modular components.

Another object of one embodiment is to provide a modular fixation system and method that utilizes a modular bridge or sleeve member that can be removably mounted onto a locking cross bar that is also used to lock a first plate to a second plate.

Still another object of one embodiment is to provide a modular bridge or sleeve member that comprises at least one anatomical or pathological characteristic, including, but not limited to, being shaped or sized in response to local anatomy or size of an interspinous space between a first spinous process and a second spinous process.

Still another object is to provide a system that method that may utilize a plurality of bridges to provide a user or surgeon the opportunity to select a bridge in response to a local anatomy prior to or at the time of surgery.

Still another object is to provide a plurality of bridges having different shapes, sizes or dimensions.

Yet another object of an embodiment is to provide a modular design that allows the user or surgeon to select a desired bridge at the time of surgery and place the bridge manually over the locking cross bar at the time of surgery.

Still another object is to provide a locking cross bar that facilitates preventing the first and second plates from separating.

Another object of an embodiment is to provide a locking cross bar that comprises a non-cylindrical shape to facilitate preventing any bridge from rotating after the bridge is mounted on the locking cross bar.

Yet another object of an embodiment is to provide a bridge and locking cross bar, at least a portion of each being adapted to be received in at least one of the first plate or second plate so that it can be locked therein.

Another object is to provide a lock that substantially simultaneously locks the first and second plates together while locking the bridge onto the locking cross bar.

Still another object is to provide a locking cross bar that has at least a portion that is tapered or ramped to facilitate preventing the first and second plates from separating.

Another object of the invention is to provide a convenient kit having a plurality of bridges and plates therein.

In one aspect, one embodiment comprises a modular interspinous fixation system comprising a first plate, a second plate, a locking cross bar for locking the first plate and the second plate together and into locked engagement with a first spinous process and a second spinous process, and a bridge for receipt on the locking cross bar, the bridge being received on the locking cross bar and becoming locked onto the locking cross bar when the locking cross bar is in the locked engagement.

In another aspect, another embodiment comprises a bridge system for use in a modular interspinous fixation system having a first plate, a second plate and a locking cross bar for coupling the first plate to the second plate to a first spinous process and a second spinous process, the bridge system comprising a plurality of bridges and each of the plurality of bridges comprising a sleeve member for slidably mounting onto the locking cross bar, each of the plurality of bridges being different in at least one of size, shape or dimension to provide a selection of bridges, at least one of the plurality of bridges being selectable by a user in response to a local anatomy including the first spinous process and the second spinous process.

In still another aspect, another embodiment comprises an interspinous fixation system comprising a first member, a second member, at least one coupling for coupling the first member to the second member and at least one bridge member for mounting on the coupling, a lock for locking the first member to the second member and to a first spinous process and a second spinous process, the at least one coupling and the at least one bridge member being adapted so that when the at least one bridge member is mounted on the at least one coupling, there is no relative rotational movement between them.

In still another aspect, another embodiment comprises a modular interspinous fixation kit comprising a plurality of plates comprising at least one first plate and at least one second plate and a plurality of bridges, each of the plurality of bridges comprising a sleeve member for slidably mounting onto at least one locking cross bar, a plurality of the plurality of bridges being different in at least one of size, shape or dimension to provide a selection of bridges at least one of which being selectable by a user in response to a local anatomy including the first spinous process and the second spinous process.

In still another aspect, another embodiment comprises a method for fusing a first spinous process to a second spinous process, the method comprising the steps of selecting a first plate, selecting a second plate, locking the first and second plates into locked engagement with the first and second spinous processes using a locking cross bar so that a bridge becomes locked between the first and second plates when the locking cross bar is in the locked engagement.

These and other objects and advantages of the invention will be apparent from the following description, the accompanying drawings and the appended claims.

DETAILED DESCRIPTION OF THE PREFERRED EMBODIMENTS

Figure 1:
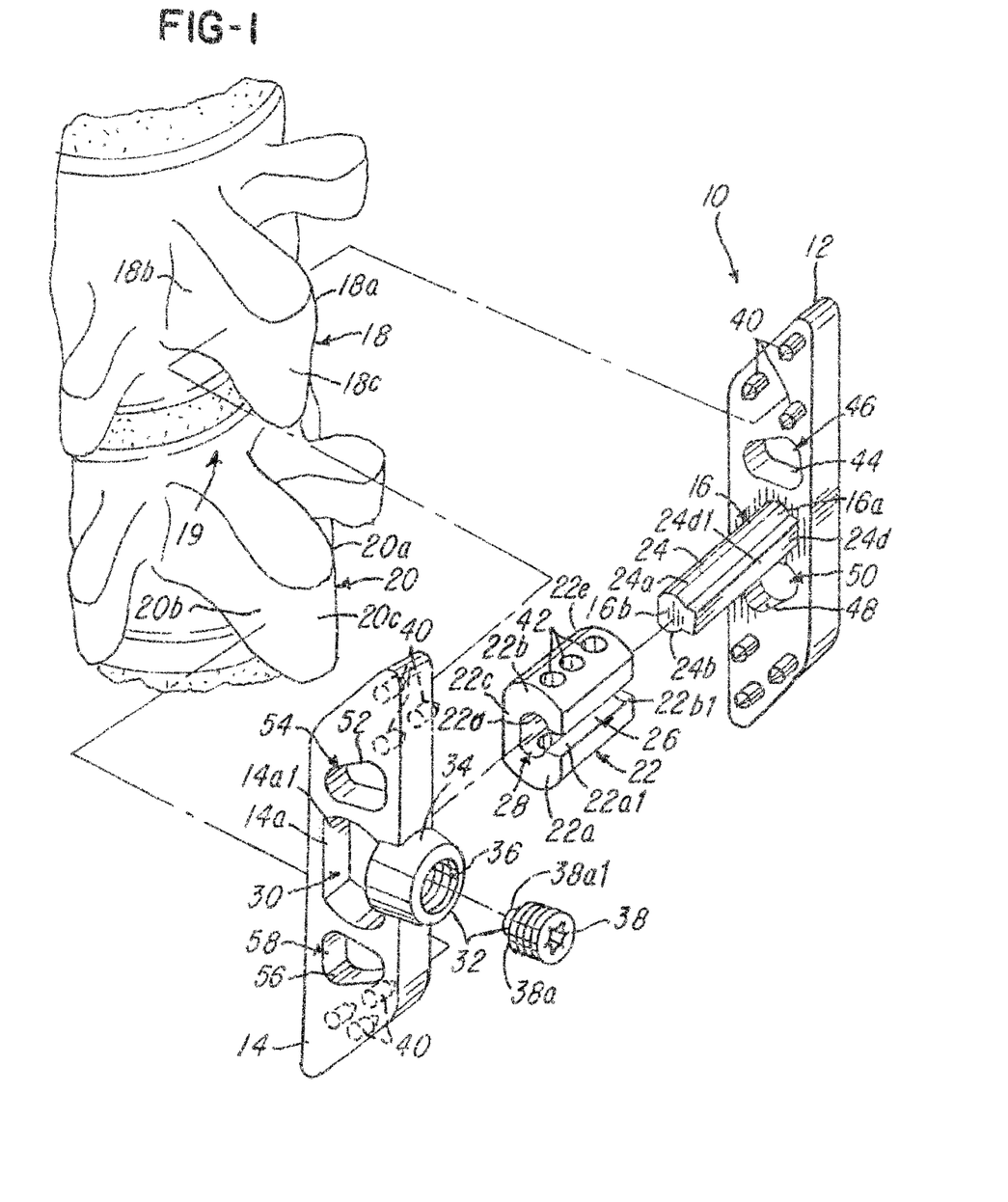
FIG. 1 is an exploded view of a modular interspinous fixation system in accordance with one embodiment of the invention.
Figure 5:
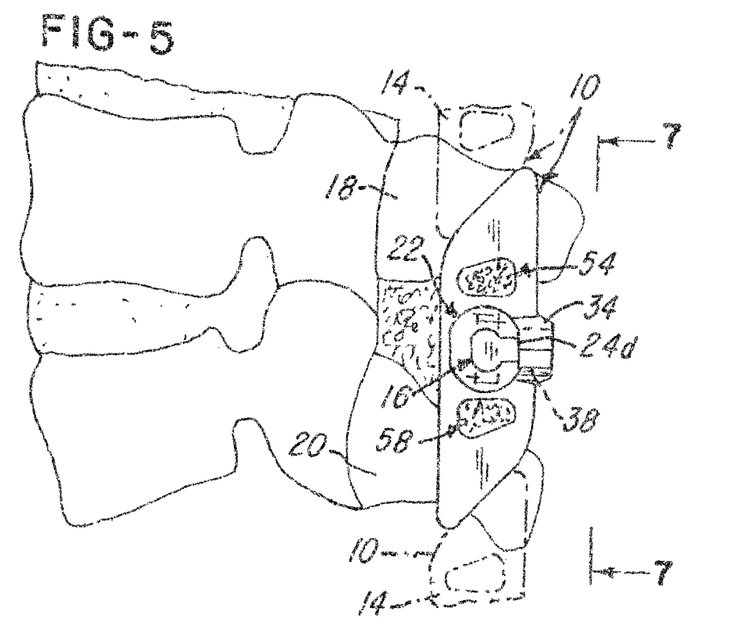
FIG. 5 is a view illustrating the modular interspinous fixation system mounted on a first spinous process and a second spinous process, with graft material inserted therebetween and illustrating a stacked arrangement of multiple modular interspinous fixation systems.

Referring now to FIG. 1, a modular interspinous fixation system 10 is shown. The modular interspinous fixation system 10 comprises a first member or plate 12 and a second member or plate 14. In the illustration being described, the first plate 12 and second plate 14 are parallelogram-like or generally shaped like a parallelogram so that they can be stacked as illustrated in FIG. 5. In one illustrative embodiment, the first plate 12 comprises at least one or a plurality of integral or monolithically formed coupling or locking cross bar 16 for locking the first plate 12 and the second plate 14 together and into a locked engagement with a first spinous process 18 and a second spinous process 20, as illustrated in FIGS. 1, 2 and 5-7.

In the illustration being described, the modular interspinous fixation system 10 further comprises a bridge 22 which is slidably or removably mounted or received on the locking cross bar 16. The locking cross bar 16 is not cylindrical in cross section, and may comprise other non-cylindrical shapes, as described later herein. The bridge 22 comprises a sleeve or sleeve member that becomes locked onto the locking cross bar 16 after it is received on the locking cross bar 16 and the locking cross bar 16 is locked or secured to the second plate 14 in the manner that will now be described.

The locking cross bar 16 comprises an elongated anti-rotation member 24 comprising a non-cylindrical shape. In the example, the elongated anti-rotation member 24 comprises a pair of curved surfaces or portions 24a and 24b and a generally planar or flat surface 24c that is integral with and couples the portions 24a and 24b together. Note that the surface 24c extends along a longitudinal length of the elongated anti-rotation member 24, and the elongated anti-rotation member 24 further comprises a radial projection or rib 24d generally opposed thereto. The radial projection or rib 24d comprises a generally planar surface 24d1 that also extends along the longitudinal length of the elongated anti-rotation member 24.

It has been found that providing the radial projection or rib 24d on the elongated anti-rotation member 24 facilitates not only preventing rotation of the rib 24d relative to the locking cross bar 16, but also orients or aligns the first plate 12 with the second plate 14. This can be advantageous during surgery where it is oftentimes difficult for the surgeon to maneuver or manipulate the first and second plates 12 and 14.

Figures 2, 3A, 3B, 4:
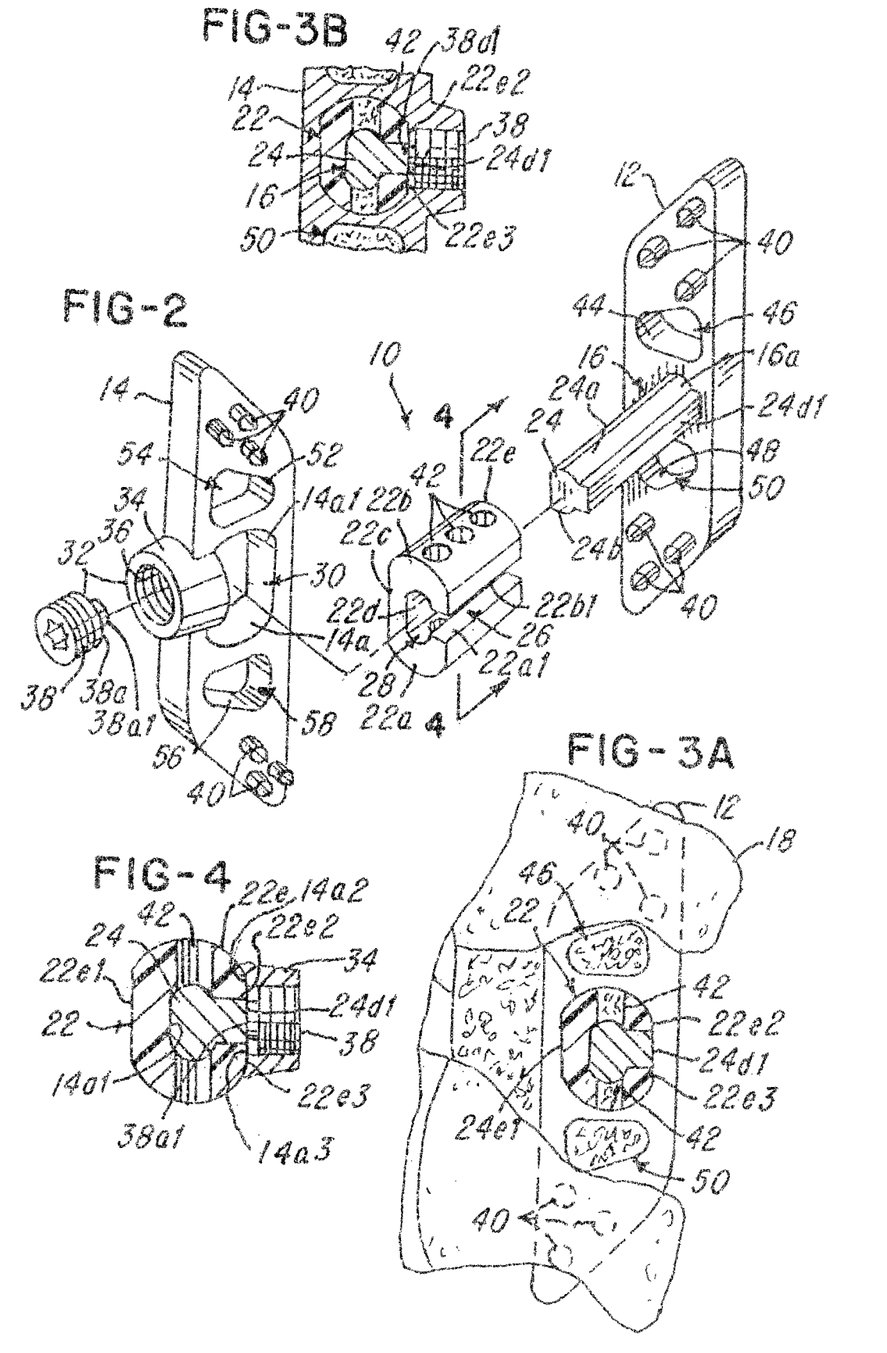
FIG. 2 is an exploded view showing various details of the embodiment shown in FIG. 1.
FIGS. 3A and 3B are sectional and fragmentary views illustrating a lock in accordance with one embodiment of the invention.
FIG. 4 is a sectional view of a sleeve member or bridge shown in FIGS. 1 and 2.

As shown in FIGS. 1 and 2, the bridge 22 is generally C-shaped as shown. The bridge 22 comprises a first generally cylindrical portion or surface 22a that comprises or terminates in a surface or wall 22a1 and a second generally cylindrical surface or portion 22b that comprises or terminates in a surface or wall 22b1. Note that the surface or wall 22b1 generally opposes the wall 22a1, and the walls 22a1 and 22b1 cooperate to define a notched-out area, opening or aperture 26 that receives the projection or rib 24d of the elongated anti-rotation member 24 of the locking cross bar 16, as illustrated in FIGS. 1-3 and 5-7.

The walls 22a1 and 22b1 cooperate to define a bridge aperture 28 having an aperture shape or dimension that complements the non-cylindrical shape or dimension of the locking cross bar 16 to facilitate preventing the bridge 22 from rotating on the locking cross bar 16.

In the illustration being described, an interior wall 22d of the bridge 22 is in communication with the walls 22a1 and 22b1. The walls 22a1, 22b1 and 22d are adapted and sized to generally complement the shape of the locking cross bar 16 so that the bridge 22 cannot rotate about its axis or relative to the locking cross bar 16.

Thus, it should be understood that the locking cross bar 16 is elongated and defines the non-cylindrical shape that comprises or adapts to comprise any shape that would facilitate reducing or eliminating rotation of the bridge 22 after the bridge 22 has been received on the locking cross bar 16.

In the illustration being described, the locking cross bar 16 comprises a first end 16a that is integrally or monolithically formed in the first plate 12 as shown. A second end 16b is blunt or truncated in the illustration shown in FIG. 1, but it could be rounded or tapered to provide a guiding nose as illustrated and described later herein relative to the embodiments shown in FIG. 8-10B. Also, the locking cross bar 16 could be non-integral with the first plate 12 as illustrated in the embodiment shown in FIG. 12, which will be described later herein.

Referring back to the illustrative embodiment shown in FIGS. 1-7, note that the second plate 14 comprises a surface or internal wall 14a that defines an aperture 30. The aperture 30 is adapted and sized to receive at least a portion of the bridge 22 and at least a portion of the locking cross bar 16 as illustrated in FIGS. 3 and 5-7. The second plate 14 further comprises a lock 32 that is in fluid communication with the aperture 30 in order to lock the at least a portion of the bridge 22 and locking cross bar 16 in the aperture 30 of the second plate 14. In one illustrative embodiment, the lock 32 comprises a female receiver 34 that has an internal threaded wall 36 for receiving a set screw 38 as shown.

Note that the internal wall 14a and aperture 30 are generally not cylindrical and are adapted and sized to generally complement the size and shape of an outer surface or wall 22e of the bridge 22 so that after the bridge 22 and locking cross bar 16 are received in the aperture 30, neither can rotate. Thus, to facilitate anti-rotation, the external surface 22e may be adapted to prevent rotation of the bridge 22 and also relative movement of the first and second plates 12 and 14. In the illustration shown in FIG. 1, for example, note that the external surface or wall 22e comprises a first generally planar portion or surface 22e1 (FIG. 4), a second generally planar portion or surface 22e2 and a third generally planar portion or surface 22e3. The first generally planar surface or portion 22e1 becomes generally opposed to and cooperates with a planar area 14a1 of wall or surface 14a, and the second and third generally planar surfaces or portions 22e2 and 22e3 become generally opposed to and cooperate with the generally planar surfaces or areas 14a2 (FIG. 3B) and 14a3, respectively, to facilitate preventing the bridge 22 from rotating. As mentioned earlier, the adaptation apertures 26 and 28 to the shape of the elongated anti-rotation member 24 of the bridge 22 and the bridge 22 in the aperture 30 facilitates proper alignment and orientation of the various components in the system 10 during the surgical procedure.

After the bridge 22 is mounted or received on the locking cross bar 16 and the bridge 22 and locking cross bar 16 are inserted into or received in the aperture 30. The generally planar surface 24d1 of projection or rib 24d lies in generally the same plane as the surfaces 22e2 (FIGS. 3A and 3B) and 22e3 and becomes co-planar therewith.

Figure 6:
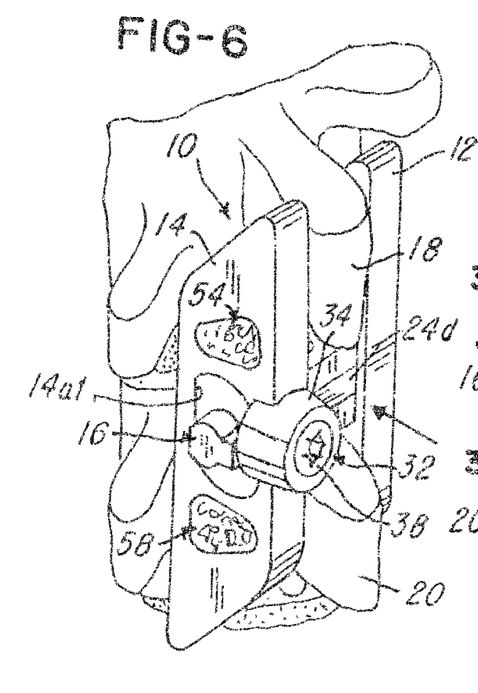
FIG. 6 is a perspective view illustrating the modular interspinous system mounted on the first and second spinous processes.
Figure 7:
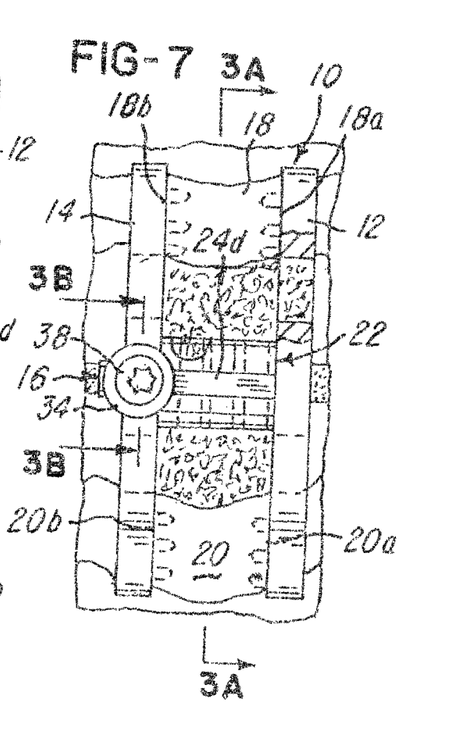
FIG. 7 is a view taken along the line 7-7 in FIG. 5 illustrating a graft area
Figures 8, 9, 10A, 10B, 11A:
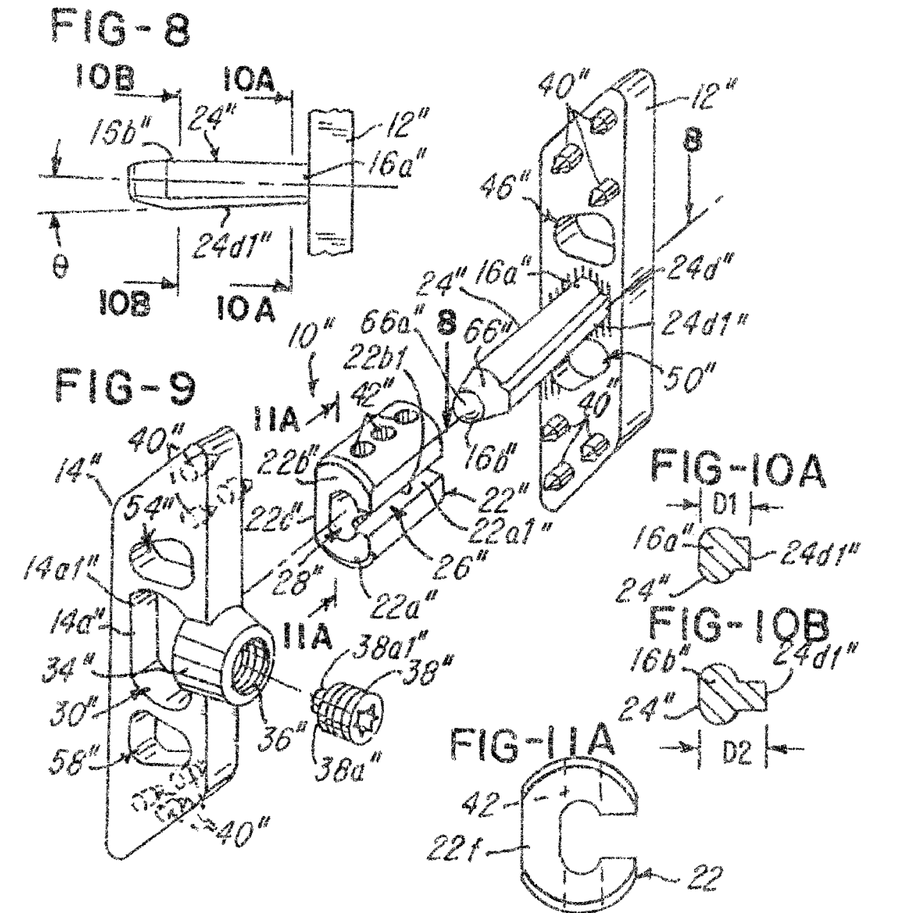
FIG. 8 is a fragmentary view showing details of a locking cross bar having a ramped or tapered surface.
FIG. 9 is an exploded view illustrating another embodiment having the ramped cross bar shown in FIG. 8
FIG. 10A is a sectional view taken along the line 10A-10A in FIG. 8.
FIG. 10B is a sectional view taken along the line 10B-10B in FIG. 8.
FIGS. 11A-11H are various end views of the sleeve member or bridge, showing various illustrative embodiments of the sleeve member or bridge having different shapes or sizes.
Figure 11B:
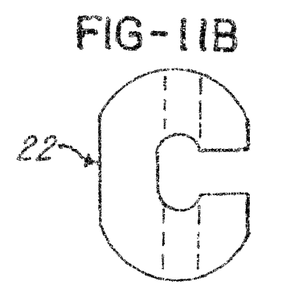
Figure 11C:
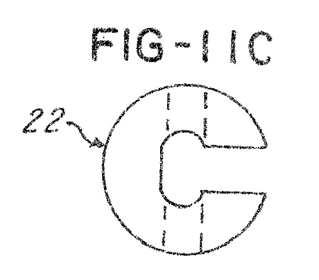
Figure 11D:
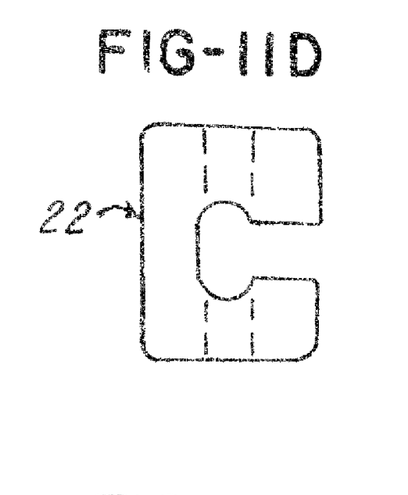
Figure 11E:
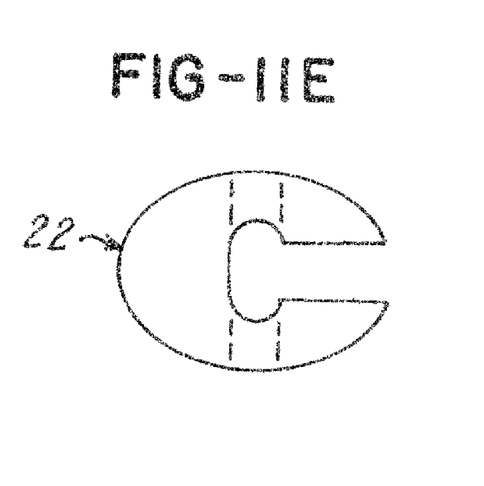
Figure 11F:
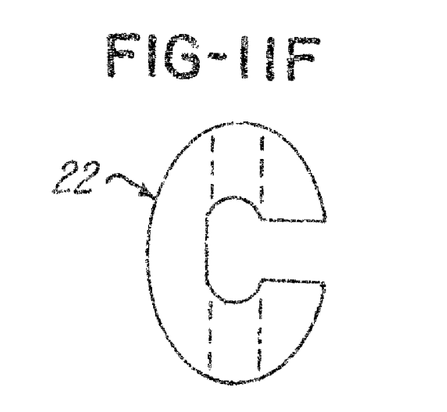
Figure 11G:
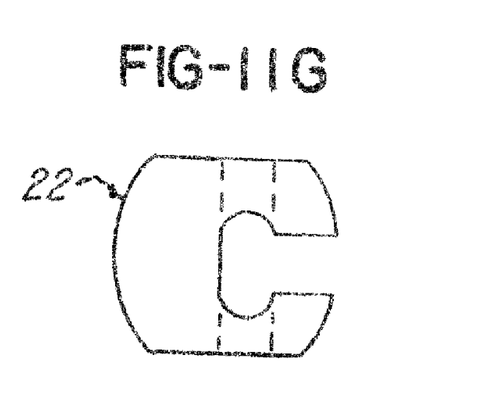
Figure 11H:
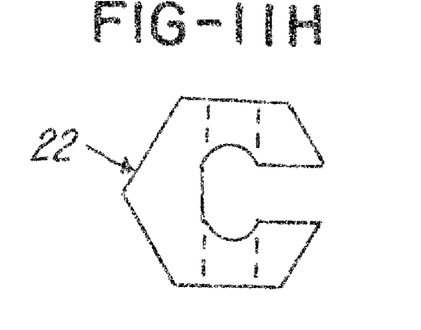

In the illustration being described, note that after the bridge 22 is mounted or received on the locking cross bar 16 and they have been received in the aperture 30, the first plate 12 and the second plate 14 are moved toward each other and into position against and capturing the first spinous process 18 and second spinous process 20 as illustrated in FIGS. 6 and 7. In this regard, the first plate 12 engages a first side 18a of the first spinous process 18 and a first side 20a of the second spinous process 20. Likewise, the second plate 14 engages the second side 18b of the first spinous process 18 and the second side 20b of the second spinous process 20. Each of the first and second plates 12 and 14 may comprise a plurality of anti-movement projections 40 that facilitate maintaining the first and second plates 12 and 14 into a secure and locked engagement with the first spinous process 18 and second spinous process 20.

After the first and second plates 12 and 14 are manually moved into position against the first and second spinous processes 18 and 20, the set screw 38 is threadably screwed in the female receiver 34 until a projection 38a1 located on an end 38a of the set screw 38 engages the surface 24d1 of the elongated anti-rotation member 24. The set screw 38 is rotated by the user or surgeon until the bridge 22 and locking cross bar 16 become locked in the aperture 30 and in the second plate 14. The user or surgeon may pre-mount the bridge 22 on the locking cross bar 16 and pre-insert the cap or set screw 38 in the internal threaded wall 36 prior to inserting them into the patient.

It should be understood that the bridge 22 is elastic and compressible so that when the projection 38a1 of the end 38a of the set screw 38 engages the surface 24d1, the axial force of the set screw 38 engaging the surface 24d1 forces the surface 24c against the planar area 14a1 of the second plate 14, and causes the bridge 22 and locking cross bar 16 to be locked in the aperture 30 of the second plate 14.

It should be understood that the sleeve member or bridge 22 may comprise a modulus of elasticity that is similar to bone or equal to or less than that of bone to facilitate avoiding overloading and/or potential fracture of at least one of the first spinous process 18 or the second spinous process 20. The sleeve member or bridge 22 may also be adapted to facilitate bone ingrowth and/or receive graft material, and one or more surfaces of the bridge 22 may be adapted, coated, treated or processed in the manner described later herein.

During use and when it is desired to fix the first spinous process 18 to the second spinous process 20, the surgeon selects the first plate 12 and the second plate 14. The surgeon then locks the first and second plates 12 and 14 into locked engagement with the first and second spinous processes 18 and 20 using the locking cross bar 16 so that the bridge 22 becomes locked between the first and second plates 12 and 14 when the locking cross bar 16 is in the locked position or engagement. If the surgeon is using the embodiment shown in FIG. 12 and described later herein, an additional step of inserting a locking cross bar 16 through an aperture 62 in the first plate 12 is performed. The step of slidably mounting the bridge 22 on the locking cross bar 16 before the locking step, with it being understood that there is no relative rotational movement between the bridge 22 and the locking cross bar 16 after the bridge 22 is mounted thereon.

After the bridge 22 is slidably received on the locking cross bar 16, the bridge 22 and locking cross bar 16 are inserted into the second plate aperture 30 in the manner described earlier herein. Thereafter, the lock 32 is actuated by rotating the set screw 38 so that the at least a portion of the bridge 22 and at least a portion of the locking cross bar 16 become locked in the aperture 30 of the second plate 14.

The surgeon may select the bridge 22 in response to a local anatomy or at least one anatomical or pathological characteristic. This at least one anatomical or pathological characteristic may include a shape or size of an interspinous space 19 between the first and second spinous processes 18 and 20.

It should be understood that the internal wall 14a of the second plate 14 that defines the aperture 30 is adapted and sized to receive at least a portion of both the locking cross bar 16 and the bridge 22 so that the lock 32 can substantially simultaneously lock the at least a portion of bridge 22 and the at least at a portion of locking cross bar 16 in the aperture 30. Notice that the bridge 22 comprises the aperture 26 which receives the projection or rib 24d to permit the set screw 38 to engage the surface 24d1 of the elongated anti-rotation member 24 of the locking cross bar 16 and the generally planar portions or surfaces 22e2 and 22e3 of the bridge 22. This engagement or locking not only prevents relative rotation to the bridge 22 and locking cross bar 16, but also locks the bridge 22 and locking cross bar 16 in aperture 30 and locks the first and second plates 12 and 14 together.

The bridge 22 may be selected from a plurality of bridges having different shapes, sizes or dimensions or that is made of different materials. For example, the bridge 22 may be made of bone, metal, sponge or a polymer. FIGS. 11A-11H show various illustrative shapes, sizes or dimensions of the bridge 22. It should be understood, however, that these shapes are merely illustrative and the bridge 22 could be adapted to comprise any suitable or desired shape, which the user or surgeon may select based upon at least one anatomized or pathological characteristic. Such characteristics may include a size or width of the interspinous space 19 (FIG. 1) as mentioned previously. For example, the surgeon may select a bridge 22 having one of the shapes illustrated in FIG. 11B, 11D or 11F for a wide interspinous space 19. In another example, if a depth of the interspinous space 19 is large, then the user or surgeon may select an elongated bridge 22 of the type shown in FIG. 11C, 11E or 11G. Thus, the bridge 22 is adapted and sized in response to at least one anatomical or pathological characteristic, which may comprise the size or shape of the interspinous space 19 (FIG. 1) between the first and second spinous processes 18 and 20.

Although not shown, the aperture 30 may be a generic shape to accommodate the different shapes of the bridge 22 or multiple second plates 14 having walls 14a that define different sized or shaped apertures 30 that complement the shapes of the external surface 22e of the bridge 22 selected may be provided. Thus, at least one or a plurality of bridges 22 may be different in at least one of size, shape or dimension to provide a selection of bridges 22, at least one of which being selectable by the user or surgeon in response to a local anatomy including the first spinous process 18 and the second spinous process 20.

In order to facilitate guiding the bridge 22 into the aperture 30 of the second plate 14, an end 22f (FIG. 11A) may have a chamfer, beveled or tapered edge or surface.

The bridge 22 may also comprise a bone ingrowth facilitator. The bone ingrowth facilitator may comprise a plurality of apertures 42 (FIGS. 2 and 4) extending at least partially or wholly through one or more of the surfaces 22a, 22b or 22c of the bridge 22 for facilitating bone ingrowth. The plurality of apertures 42 may also provide areas for receiving graft material which is placed between the first and second plates 12 and 14, as illustrated in FIG. 7.

The external surfaces 22a, 22b and 22c of the bridge 22 could also define the bone ingrowth facilitator in that it could comprise a coating that facilitates bone ingrowth, such as a hydroxyapatite coating. Also, the surfaces 22b-22e could be adapted to facilitate bone ingrowth by sintering, surface etching, surface machining, surface blasting, drilling, trabecular composition or by providing the apertures 42 mentioned earlier herein. As mentioned earlier, the bridge 22 could also be made of a metal, sponge, bone or a polymer.

The first and second plates 12 and 14 may comprise one or more graft windows for inserting graft material into the interspinous are 19. In this regard, the first plate 12 may comprise a first wall 44 that defines a first graft window 46 and a second wall 48 that defines a second graft window 50. Likewise, the second plate 14 may comprise a first wall 52 that defines a first graft window 54 and a second wall 56 that defines a second graft window 58. After the first and second plates 12 and 14 are mounted onto the first and second spinous processes 18 and 20 as described earlier herein, the graft material may be inserted using the graft windows 46, 50, 54 and 58 or may be inserted in the direction of arrow A (FIG. 6) until the interspinous space 19 and the apertures 42 and areas between the first and second spinous processes 18 and 20 have received the graft material.

It should be understood that the components of the modular interspinous fixation system 10 may comprise different materials. For example, the locking cross bar 16 and bridge 22 may be made of different materials. In one illustrative embodiment, the locking cross bar 16 and first and second plates 12 and 14 could be made of a metal, while the bridge 22 is made of a polymer.

Figure 12:
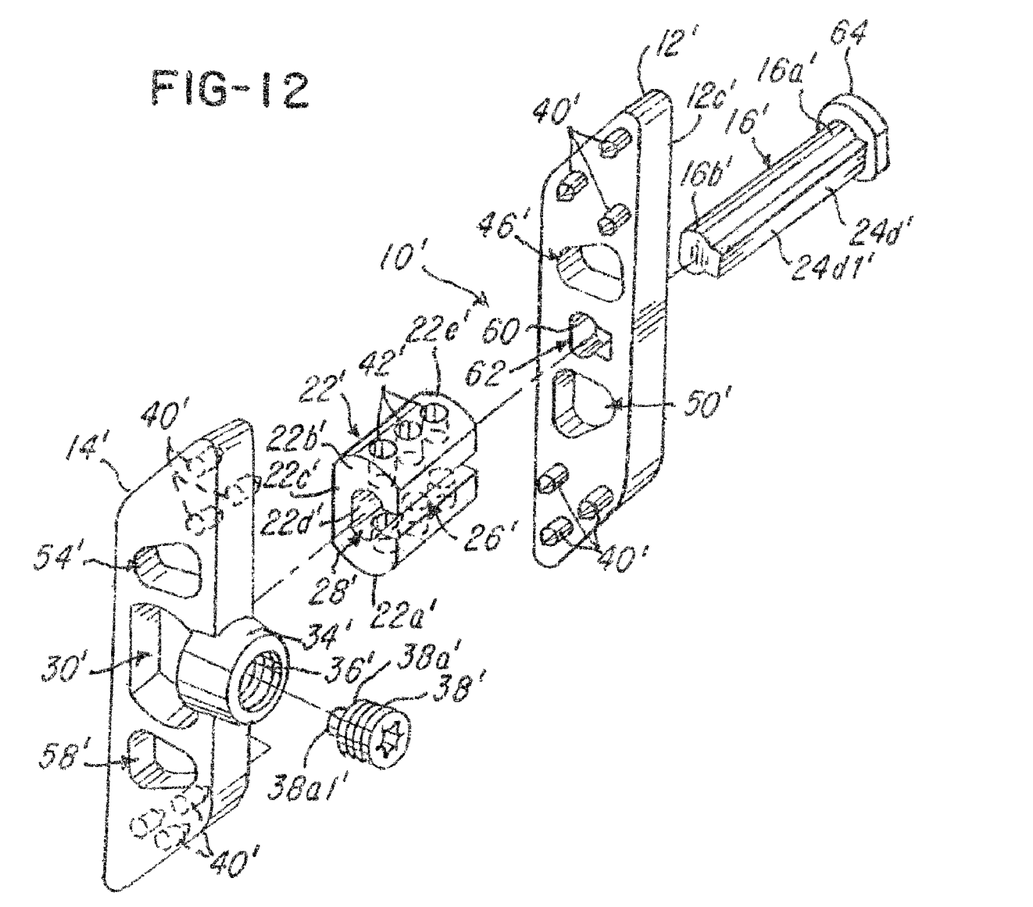
FIG. 12 is an exploded view of another embodiment illustrating a non-integral locking cross bar that is inserted through the first plate.

Referring now to FIG. 12, another embodiment is shown. Those parts that are the same or similar to the parts shown and described earlier herein relative to FIGS. 1-7 bear the same part number, except that an apostrophe ("'") has been added to the part number in FIG. 12.

As mentioned earlier herein, the embodiment shown and described relative to FIGS. 1-7 comprise the locking cross bar 16 having the end 16a that is monolithically formed in or integral with the first plate 12. In contrast, the embodiment shown in FIG. 12 shows the locking cross bar 16 that is not integral with the first plate 12. The first plate 12 comprises an internal wall 60 that defines an aperture 62 that is adapted and sized to complement the shape of the locking cross bar 16. In this illustration, the locking cross bar 16 is inserted through the aperture 60 until a generally planar head 64 engages a side wall 12c of the first plate 12. The head 64 is integrally formed with the end 16a of the locking cross bar 16. In the illustration being described and as shown and described later herein relative to FIG. 14, the system 10 may comprise a plurality of first plates 12 and a plurality of locking cross bars having different lengths. The user or surgeon may select a first plate 12 and locking cross bar 16 in response to the distance between the first plate 12 and second plate 14 after the first and second plates 12 and 14 are placed into engagement with the first and second spinous processes 18 and 20.

FIGS. 8-10B illustrate still another embodiment of the invention. In this embodiment, like parts are identified with the same part numbers, except that a double prime mark ("''") has been added to the part numbers for the parts in FIGS. 8-10B.

Note that in the embodiment in FIGS. 8-10B, the surface 24d1" and projection or rib 24d" of locking cross bar 16" is tapered or ramped, as illustrated FIGS. 8-10B. Thus, note in the cross section view in FIG. 10A, a distance D1 is smaller than the distance D2 (FIG. 10B) for a cross section taken toward the end 16b" of the locking cross bar 16". Note in FIG. 8 that the surface 24d1" of the elongated anti-rotation member 24" is tapered or ramped at an angle θ. In one illustrative embodiment, the slope or angle θ is approximately 1.58 degrees, but it could assume other angles as well. The slope, taper and ramping of the locking cross bar 16" adds extra locking security to prevent separation of the first plate 12" and second plate 14" under high load after the set screw 38" has been locked. In other words, after the set screw 38" has been locked down onto the locking cross bar 16", additional force would be necessary to pull the first and second plates 12" and 14" apart because of the increasing cross sectional width or dimension of the locking cross bar 16".

Another feature of the embodiment illustrated in FIGS. 8-10C, which could also be used in the embodiments shown and described relative to FIGS. 1-7 and 12, is the beveled or tapered nose 66" (FIG. 9) at the end 16b". Note that the surfaces 66" are rounded or tapered to facilitate inserted the locking cross bar 16" into the aperture 28" of bridge 22", and for the illustration shown in FIG. 12, the aperture 60". Either prior to or during a surgical procedure, it may be necessary to insert the locking cross bar 16, 16 or 16" into the bridge 22", and the tapered nose 66" can facilitate guiding the locking cross bar 16" into the bridge 22".

Figures 13, 14:
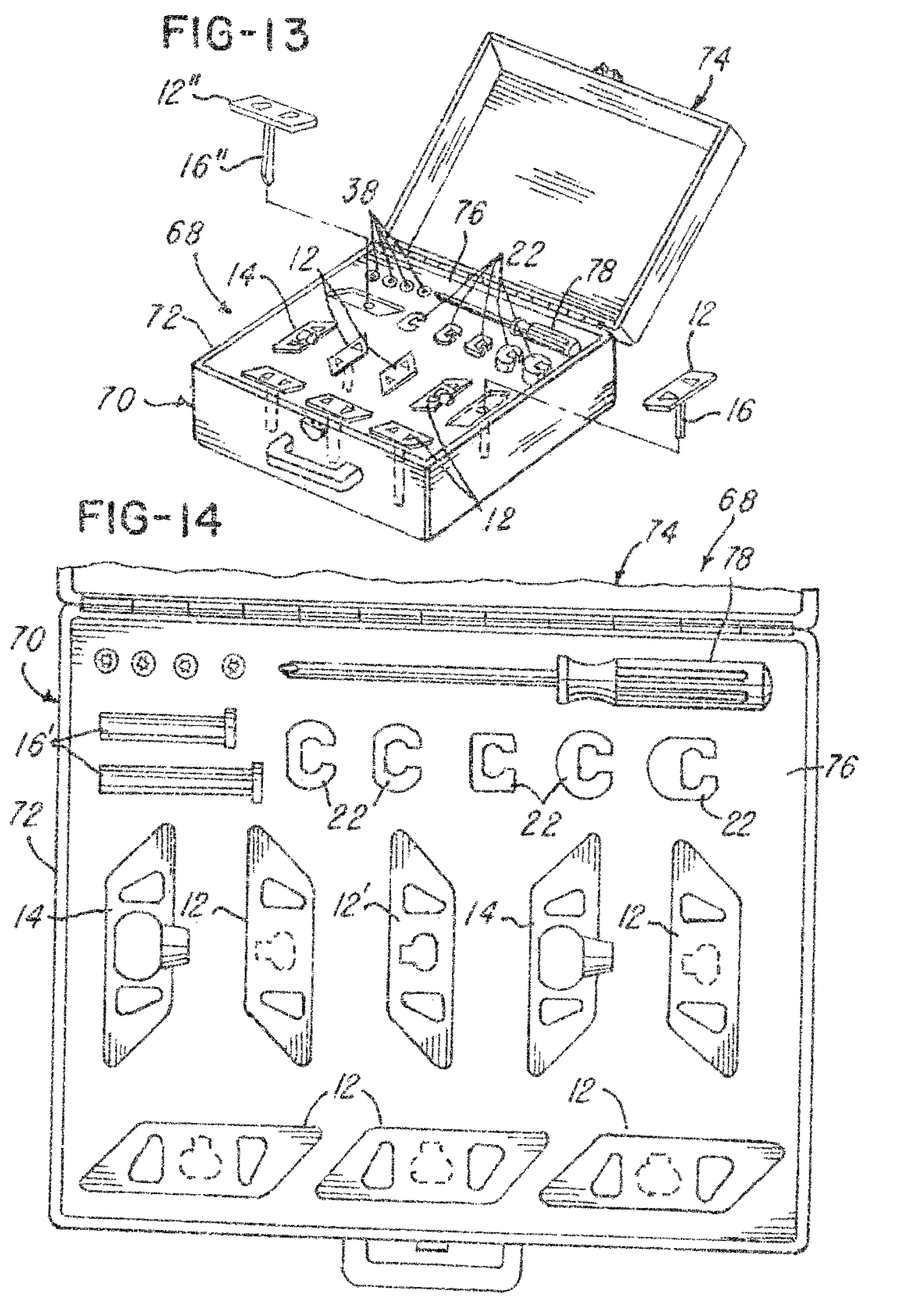
FIG. 13 is a perspective view of an illustrative kit in which the various modular components of the embodiments shown in FIGS. 1-11H.
FIG. 14 is a fragmentary plane view of another kit for use with the embodiment illustrated in FIG. 12.

The system 10 may be provided in at least one or a plurality of kits 68 (FIGS. 13 and 14). FIGS. 13 and 14 illustrate the modular components of the system 10 provided in a container or case 70 having a bottom 72 and a lid 74 which is hingeably attached to the bottom 72. In the illustration being described, the bottom 72 is filled with a foam 76, such as Styrofoam, having a plurality of cut-outs adapted and sized to receive and store the various components of the system 10 as shown. Note that a plurality of different size and shape bridges 22 are provided with the first and second plates 12, 12" and 14, 14" described relative to the embodiment shown in FIGS. 1-7 and 8-12.

FIG. 14 illustrates a similar case 70 used to house the modular components of the embodiment shown relative to FIG. 12. As illustrated in FIG. 13, the kit 68 could be used to house the modular components of the embodiment illustrated and described earlier herein relative to FIGS. 8-10B. Note that the kits 68 in FIGS. 13 and 14 may comprise one or more tools, such as a screw driver 78 for driving the set screw 38.

Advantageously, the system 10 provides a modular interspinous fixation system that provides various features and advantages, used alone or in combination, including, but not limited to:

providing rigid fixation of adjacent vertebral spinous processes for the purpose of attaining a bony fusion, rather than loosely or dynamically spacing the spinous processes apart;

achieving stabilization under movements of flexion, extension, rotation and lateral bending;

containing a modular, non-rotatable, central bridging portion or bridge 22 which can be selected for both size and biological properties to address anatomy and pathology;

containing a lock or locking system which functions to both stabilize the central bridging portion and simultaneously locks the device or system 10 onto the adjacent spinous processes;

containing a locking mechanism that utilizes metal on metal locking surfaces even if the central bridging portion is polymer or other non-metallic or non-solid composition;

containing a locking crossbar which functions to simultaneously anchor the central bridging portion in a non-rotatable fashion and provides a locking surface for the locking mechanism;

incorporating a central bridging portion or bridge 22 which incorporates features for bony ingrowth, such as by example, hydroxyapatite coating, surface sintering, surface etching, surface machining, surface blasting, drilling, or trabecular composition;

incorporating a central bridging portion or bridge 22 which is manufactured from polymer to achieve a modulus of elasticity similar to bone so as to avoid overloading and potential fracture of the spinous process;

incorporating a central bridging portion or bridge 22 which is available in a selection of sizes to conform to local anatomy;

incorporating a central bridging portion or bridge 22 with a central aperture and communicating notch to allow for locking of the locking crossbar through said bridging portion;

a modular design which allows for the surgeon to select the desired central bridging portion or bridge 22 at the time of surgery and place the central bridging portion manually over the locking crossbar at the time of surgery;

incorporating the modular components into a convenient kit for use by the surgeon at the time of surgery;

providing a locking cross bar 16 that facilitates retaining the first plate 12 and second plate 14 together by providing a ramped portion that facilitates preventing the first and second plates 12 and 14 from separating and/or causes them to be urged together when the set screw 38 is screwed to the locked position; and providing a system 10 that has a plurality of bridges 22 having different shapes and/or sizes that enables the surgeon to select an appropriately-sized bridge 22 in response to the size of the interspinous space 19.

Although not shown, multiple pairs of plates may be provided and mounted onto the spinal column as illustrated in phantom in FIG. 5. Also, while it is not preferred, multiple bridges 22 could be simultaneously received on the locking cross bar 16. Also, the embodiments illustrated in FIG. 1-14 illustrate a single locking cross bar 16, but it should be understood that multiple locking cross bars 16 could be utilized. Various different locking cross bars 16, 16 and 16" may be utilized separately or together when multiple locking cross bars 16, 16 and 16" are used.

While the system and method herein described, and the various embodiments shown and described, constitute several preferred embodiments of this invention, it is to be understood that the invention is not limited to this precise system, method and embodiments, and that changes may be made in any of them without departing from the scope of the invention, which is defined in the appended claims.

What is claimed is:

1. A modular interspinous fixation system comprising:
a first plate;
a second plate;
a locking cross bar for locking said first plate and said second plate together and into locked engagement with a first spinous process and a second spinous process; and
a bridge for receipt on said locking cross bar;
said second plate having a second plate aperture, said bridge extending into said second plate aperture and through said second plate, when said first and second plates are secured together with said locking cross bar;
said bridge being received on said locking cross bar and becoming locked onto said locking cross bar when said locking cross bar is in said locked engagement.

2. The modular interspinous fixation system as recited in claim 1 wherein said locking cross bar is elongated and defines a non-cylindrical shape in cross section, said bridge having a bridge aperture having an aperture shape that complements said non-cylindrical shape to facilitate preventing said bridge from rotating on said locking cross bar.

3. The modular interspinous fixation system as recited in claim 1 wherein said locking cross bar comprises an end that is integral with at least one of said first plate or said second plate.

4. The modular interspinous fixation system as recited in claim 1 wherein said locking cross bar has a portion that is tapered or ramped along its length.

5. The modular interspinous fixation system as recited in claim 1 wherein said locking cross bar comprises a first end that is integral with said first plate,
said second plate having a second plate aperture for receiving a second end of said locking cross bar;
said second plate having a lock associated with said second plate aperture for locking said locking cross bar in said second plate.

6. The modular interspinous fixation system as recited in claim 5 wherein said second plate aperture is adapted and sized to receive both said locking cross bar and said bridge.

7. The modular interspinous fixation system as recited in claim 5 wherein said second plate aperture is adapted and sized to receive both said locking cross bar and said bridge, said lock substantially simultaneously locking said bridge and said locking cross bar in said second plate aperture.

8. The modular interspinous fixation system as recited in claim 7 wherein said second plate comprises a wall for defining said second plate aperture, said lock comprising a set screw and said bridge comprising an opening for permitting said set screw to engage at least one of said locking cross bar or said bridge, said set screw cooperating with said wall to lock at least a portion of said bridge and said locking cross bar therebetween.

9. The modular interspinous fixation system as recited in claim 8 wherein said locking cross bar and said bridge are made of different materials.

10. The modular interspinous fixation system as recited in claim 9 wherein said locking cross bar is metal and said bridge is a polymer.

11. The modular interspinous fixation system as recited in claim 1 wherein said bridge is adapted and sized in response to at least one anatomical or pathological characteristic.

12. The modular interspinous fixation system as recited in claim 11 wherein said at least one anatomical or pathological characteristic comprises a size of an interspinous space between said first spinous process and said second spinous process.

13. The modular interspinous fixation system as recited in claim 1 wherein said bridge comprises a plurality of apertures for receiving bone or graft material for facilitating fusion of said first spinous process to said second spinous process.

14. The modular interspinous fixation system as recited in claim 1 wherein said locking cross bar comprises an external surface that is adapted and shaped to receive said bridge such that there is no relative movement between said bridge and said locking cross bar.

15. The modular interspinous fixation system as recited in claim 1 wherein said bridge comprises at least one surface comprising a bone ingrowth facilitator.

16. The modular interspinous fixation system as recited in claim 15 wherein said bone ingrowth facilitator comprises a hydroxyapatite coating, surface sintering, surface etching, surface machining, surface blasting, drilling, or trabecular composition.

17. The modular interspinous fixation system as recited in claim 1 wherein said bridge comprises a modulus of elasticity of bone equal to or less than a modulus of elasticity of to facilitate avoiding overloading and/or potential fracture of at least one of said first spinous process or said second spinous process.

18. The modular interspinous fixation system as recited in claim 1 wherein said system comprises a second bridge adapted to be mounted on said locking cross bar, said second bridge being of a different size or shape than said bridge.

19. The modular interspinous fixation system as recited in claim 1 wherein said system comprises a plurality of bridges, said plurality of bridges being different in at least one of size, shape or dimension to provide a selection of bridges at least one of which being selectable by a user in response to a local anatomy including said first spinous process and said second spinous process.

20. The modular interspinous fixation system as recited in claim 1 wherein said bridge comprises an aperture and a notched-out area in communication with said aperture to allow for sliding said locking cross bar into said aperture and said notched-out area of said bridge.

21. The modular interspinous fixation system as recited in claim 1 wherein said locking cross bar is adapted to receive at least one of a plurality of bridges, each of said plurality of bridges being of a different size or shape, thereby enabling a user to select at least one of said plurality of bridges at a time for implantation when said first and second plates are locked to said first and second spinous processes.

22. The modular interspinous fixation system as recited in claim 1 wherein said system further comprises a lock for locking at least a portion of said bridge and at least a portion of said locking cross bar, said first plate and second plate together.

23. The modular interspinous fixation system as recited in claim 22 wherein said lock comprises a set screw threadably mounted in said first plate or said second plate.

24. The modular interspinous fixation system as recited in claim 1 wherein said bridge comprises an outer surface generally defining a predetermined shape.

25. The modular interspinous fixation system as recited in claim 24 wherein said predetermined shape comprises at least a portion that is arcuate, a polygonal, or non-cylindrical.

26. The modular interspinous fixation system as recited in claim 1 wherein said bridge is generally C-shaped in cross section.

27. The modular interspinous fixation system as recited in claim 1 wherein said bridge is not cylindrical about its axis and comprises a wall thickness that is not constant about its axis.

28. The modular interspinous fixation system as recited in claim 1 wherein said bridge comprises a notched-out area that extends along a longitudinal length of said bridge.

29. The modular interspinous fixation system as recited in claim 1 wherein said bridge is made of metal, sponge, bone, or a polymer.

30. The modular interspinous fixation system as recited in claim 1 wherein said locking cross bar comprises an elongated portion having a first end and a second end;
said elongated portion having a projection having a flat or planar surface;
said bridge having a first wall and a generally opposed second wall that cooperate to define a notched-out area adapted to receive said projection when said bridge is mounted on said locking cross bar.

31. The modular interspinous fixation system as recited in claim 30 wherein said elongated portion comprises a generally cylindrical portion, said generally cylindrical portion being integrally formed with said projection, said bridge comprises a bridge aperture that is in communication with said notched-out area, said bridge aperture receiving said generally cylindrical portion and said notched-out area receiving said projection when said bridge is mounted on said locking cross bar.

32. The modular interspinous fixation system as recited in claim 30 wherein said first end of said elongated portion comprises a head, said first plate comprising a first wall defining a first plate aperture for receiving said elongated portion until said head engages said first plate, said second plate having a second plate wall that defines a second plate aperture that is adapted to receive both said bridge and said elongated portion after said bridge is mounted thereon, said second plate comprising a threaded aperture in communication with said second plate aperture for receiving a screw so that when said first and second plates are situated on said first and second spinous processes and said screw is screwed into said threaded aperture, said screw engages said flat or planar surface, thereby locking said first plate and said second plate to said first and second spinous processes and also locking said bridge and said elongated portion to said second plate.

33. The modular interspinous fixation system as recited in claim 30 wherein said first end is integrally formed in said first plate, said second plate having a second plate wall that defines a second plate aperture that is adapted to receive both said bridge and said elongated portion after said bridge is mounted thereon, said second plate comprising a threaded aperture in communication with said second plate aperture for receiving a screw so that when said first and second plates are situated on said first and second spinous processes and said screw is screwed into said threaded aperture, said screw engages said flat or planar surface, thereby locking said first plate and said second plate to said first and second spinous processes and also locking said bridge and said elongated portion to said second plate.

34. The modular interspinous fixation system as recited in claim 1 wherein said first and second plates each comprise at least one graft window.

35. The modular interspinous fixation system as recited in claim 1 wherein said first and second plates each comprise a plurality of engagement teeth for engaging said first and second spinous processes when said first and second plates are mounted to said first and second spinous processes.

36. The modular interspinous fixation system as recited in claim 1 wherein said first and second plates each have a perimeter wall generally defining a parallelogram.

37. The modular interspinous fixation system as recited in claim 1 wherein said system further comprises a plurality of locking cross bars of differing lengths, said locking cross bar being selected from said plurality of locking cross bars in response to a distance between said first plate and said second plate after they are placed in engagement with said first spinous process and said second spinous process.

38. The modular interspinous fixation system as recited in claim 1 wherein said second plate aperture is adapted and sized to receive both said bridge and said locking cross bar when said first and second plates are secured together.

39. A modular interspinous fixation system comprising:
a first plate;
a second plate;
a locking cross bar for locking said first plate and said second plate together and into locked engagement with a first spinous process and a second spinous process; and
a bridge for receipt on said locking cross bar;
said bridge being received on said locking cross bar and becoming locked onto said locking cross bar when said locking cross bar is in said locked engagement;
wherein said locking cross bar comprises an external surface that is adapted and shaped to receive said bridge such that there is no relative movement between said bridge and said locking cross bar wherein said locking cross bar is in said locked engagement;
wherein said locking cross bar comprises a projection or rib having a screw contact area, said bridge having an inner bridge wall that defines a bridge aperture for receiving said projection or rib;
said second plate having a second plate wall defining a locking cross bar aperture, said locking cross bar aperture receiving said locking cross bar and at least a portion of said bridge after said bridge is mounted on said locking cross bar and said bridge and said locking cross bar are received in said locking cross bar aperture;
said second plate further comprising a threaded opening that is generally aligned with said screw contact area so that when a screw is threadably received in said threaded opening, said screw may engage said screw contact area in order to lock said bridge and said locking cross bar in said second plate.

40. The modular interspinous fixation system as recited in claim 39 wherein said screw contact area is generally flat or planar.

41. An interspinous fixation system comprising:
a first member;
a second member, said second member comprising a second member wall for defining a second member aperture;
at least one coupling for coupling said first member to said second member; and,
at least one bridge member for mounting on said coupling;
said at least one coupling and said at least one bridge member being adapted so that when said at least one bridge member is mounted on said at least one coupling, there is no relative rotational movement between them and extends into said second member aperture and through said second member said second member having a lock for locking said bridge members in said second member aperture so that said bridge member is captured in said second member.

42. The interspinous fixation system as recited in claim 41 wherein said at least one bridge member is a sleeve that is slidably mounted on said at least one coupling before said first and second members are secured together.

43. The interspinous fixation system as recited in claim 42 wherein said at least one coupling comprises an elongated cross bar having a first end coupled to said first member and a second end coupled to said second member.

44. The interspinous fixation system as recited in claim 43 wherein said elongated cross bar is non-cylindrical in cross section, said at least one bridge member comprising a bridge wall that defines a bridge aperture for receiving said elongated cross bar, said bridge aperture comprising a shape that generally complements said non-cylindrical shape of said cross section so that when said at least one bridge member is mounted on said at least one coupling, there is no relative rotational movement therebetween.

45. The interspinous fixation system as recited in claim 41 wherein said second member wall that defines a locking aperture for simultaneously receiving said at least one coupling and said at least one bridge member together, said second member further comprising a screw associated with said locking aperture for engaging at least one of said at least one coupling or said at least one bridge member in order to lock them in said locking aperture.

46. The interspinous fixation system as recited in claim 45 wherein said at least one coupling comprises a coupling projection that comprises a generally flat or planar surface, said at least one bridge member comprising at least one aperture that becomes generally aligned with said generally flat or planar surface after said at least one bridge member is mounted on said at least one coupling so that said screw can engage said at least one coupling and secure both it and said at least one bridge member against said wall.

47. The interspinous fixation system as recited in claim 41 wherein said at least one coupling comprises an elongated member having an end that is integral with at least one of said first member or said second member.

48. The interspinous fixation system as recited in claim 41 wherein said at least one coupling comprises an elongated member having a first end that is integral with said first member;
said second member aperture for receiving a second end of said elongated member;
said second member having a lock associated with said second member aperture for locking said elongated member in said second member.

49. The interspinous fixation system as recited in claim 48 wherein said second member aperture is adapted and sized to receive both said first end and said second end of said elongated member and at least a portion of said at least one coupling, said lock substantially simultaneously locking said at least one coupling and said elongated member in said second member aperture.

50. The interspinous fixation system as recited in claim 49 wherein said second member comprises a second member wall for defining said second member aperture, said lock comprising a set screw and said at least one bridge member comprising an opening for receiving said set screw and permitting said set screw to engage said at least one coupling, said set screw cooperating with said wall to lock at least a portion of said at least one bridge member and said at least one coupling therebetween.

51. The interspinous fixation system as recited in claim 41 wherein said at least one coupling and said at least one bridge member are made of different materials.

52. The interspinous fixation system as recited in claim 51 wherein at least one coupling is metal and said at least one bridge member is a polymer.

53. The interspinous fixation system as recited in claim 41 wherein said at least one bridge member is adapted and sized in response to at least one anatomical or pathological characteristic.

54. The interspinous fixation system as recited in claim 53 wherein said at least one anatomical or pathological characteristic comprises a size of an interspinous space between a first spinous process and a second spinous process.

55. The interspinous fixation system as recited in claim 41 wherein said at least one bridge member comprises a plurality of graft apertures for receiving graft material and facilitating fusion of a first spinous process to a second spinous process.

56. The interspinous fixation system as recited in claim 41 wherein said at least one coupling comprises an external surface that is adapted and shaped to receive said at least one bridge member such that there is no relative movement between said at least one bridge member and said at least one coupling.

57. The interspinous fixation system as recited in claim 41 wherein said at least one coupling comprises a surface that is tapered or ramped.

58. The interspinous fixation system as recited in claim 41 wherein said at least one bridge member comprises at least one surface comprising a bone ingrowth facilitator.

59. The interspinous fixation system as recited in claim 58 wherein said bone ingrowth facilitator comprises a hydroxyapatite coating, surface sintering, surface etching, surface machining, surface blasting, drilling, or trabecular composition.

60. The interspinous fixation system as recited in claim 41 wherein said at least one bridge member comprises a modulus of elasticity of equal to or less than a modulus of elasticity of a first spinous process and a second spinous process to facilitate avoiding overloading and/or potential fracture of at least one of said first spinous process or said second spinous process.

61. The interspinous fixation system as recited in claim 41 wherein said system comprises a plurality of bridge members, said plurality of bridge members being different in at least one of size, shape or dimension to provide a selection of bridge members, at least one of which being selectable by a user in response to a local anatomy including a first spinous process and a second spinous process.

62. The interspinous fixation system as recited in claim 41 wherein said at least one bridge member comprises an outer surface generally defining a predetermined shape.

63. The interspinous fixation system as recited in claim 62 wherein said predetermined shape defines at least a portion of that is arcuate, a polygonal, or non-cylindrical.

64. The interspinous fixation system as recited in claim 41 wherein said at least one bridge member is generally C-shaped in cross section.

65. The interspinous fixation system as recited in claim 41 wherein said at least one bridge member is not cylindrical about its axis and comprises a wall thickness that is not constant about its axis.

66. The interspinous fixation system as recited in claim 41 wherein said at least one bridge member comprises a notched-out area that extends along a longitudinal length of said at least one bridge member.

67. The interspinous fixation system as recited in claim 41 wherein said at least one bridge member is made of sponge, bone, or a polymer.

68. The interspinous fixation system as recited in claim 41 wherein said at least one coupling comprises an elongated portion having a first end and a second end;
said elongated portion having a radial projection having a flat or planar surface;
said at least one bridge member having a first wall and a generally opposed second wall that cooperate to define a notched-out area adapted to receive said projection when said at least one bridge member is mounted on said at least one coupling.

69. The interspinous fixation system as recited in claim 68 wherein said elongated portion comprises a generally cylindrical portion, said generally cylindrical portion being integrally formed with said projection, said at least one bridge member comprises at least one bridge member aperture that is in communication with said notched-out area, said at least one bridge member aperture receiving said generally cylindrical portion and said notched-out area receiving said projection when said at least one bridge member is mounted on said at least one coupling.

70. The interspinous fixation system as recited in claim 68 wherein said first end of said elongated portion comprises a head, said first member comprising a first wall defining a first member aperture for receiving said elongated portion until said head engages said first member, said second member having a second member wall that defines a second member aperture that is adapted to receive both said at least one bridge member and said elongated portion after said at least one bridge member is mounted or received on said elongated portion, said second member comprising a threaded aperture in communication with said second member aperture for receiving a screw so that when said first and second members are situated on first and second spinous processes and said screw is screwed into said threaded aperture, said screw engages said flat or planar surface, thereby locking said first member and said second member to said first and second spinous processes and also locking said at least one bridge member and said elongated portion to said second member.

71. The interspinous fixation system as recited in claim 68 wherein said first end is integrally formed in said first member, said second member having a second member wall that defines a second member aperture that is adapted to receive both said at least one bridge member and said elongated portion after said at least one bridge member is mounted thereon, said second member comprising a threaded aperture in communication with said second member aperture for receiving a screw so that when said first and second members are situated on first and second spinous processes and said screw is screwed into said threaded aperture, said screw engages said flat or planar surface, thereby locking said first member and said second member to said first and second spinous processes and also locking said at least one bridge member and said elongated portion to said second member.

72. The interspinous fixation system as recited in claim 41 wherein said first and second members each comprise at least one graft window.

73. The interspinous fixation system as recited in claim 41 wherein said first and second members each comprise a plurality of engagement teeth for engaging said first and second spinous processes when said first and second members are mounted to first and second spinous processes.

74. The interspinous fixation system as recited in claim 41 wherein said first and second members each have a perimeter wall that is generally parallelogram-like.

75. The interspinous fixation system as recited in claim 41 wherein said second member is adapted and sized to receive both said bridge member and said coupling when said first and second members are secured together.

76. An interspinous fixation system comprising:
a first member;
a second member;
at least one coupling for coupling said first member to said second member;
at least one bridge member for mounting on said coupling: and
a lock for locking said first member to said second member and to a first spinous process and a second spinous process;
said at least one coupling and said at least one bridge member being adapted so that when said at least one bridge member is mounted on said at least one coupling, there is no relative rotational movement between them;
wherein said at least one coupling comprises a surface that is tapered or ramped; wherein said at least one coupling comprises a projection having a contact area, said at least one bridge member having a bridge member wall that defines a bridge member aperture for receiving said projection;
said second member having a second member wall defining at least one coupling aperture, said at least one coupling aperture receiving said at least one coupling and at least a portion of said at least one bridge member after said at least one bridge member is mounted on said at least one coupling and said at least one bridge member and said at least one coupling are received in said at least one coupling aperture;
a threaded opening becoming generally aligned with said contact area so that when a screw is threadably received in said threaded opening, said screw may engage said contact area in order to lock said at least one bridge member and said at least one coupling in said second member.

77. The interspinous fixation system as recited in claim 76 wherein said contact area is generally flat or planar and comprises said surface that is tapered or ramped.

78. A method for fusing a first spinous process to a second spinous process, said method comprising the steps of:
selecting a first plate;
selecting a second plate, said second plate comprising a second plate aperture extending therethrough;
slidably mounting a bridge on said locking cross bar;
sliding said bridge and a locking cross bar, said bridge being received in said second plate;
locking said first and second plates into locked engagement with said first and second spinous processes using said locking cross bar, said bridge passing into said second plate aperture and through said second plate and becoming locked thereto when said first and second plates are in said locked engagement.

79. The method as recited in claim 78 wherein said method further comprises the step of:
slidably mounting said bridge on said locking cross bar before said locking step, there being no relative rotational movement between said bridge and said locking cross bar after said bridge is mounted thereon.

80. The method as recited in claim 79 wherein said locking cross bar is elongated and defines a non-cylindrical shape in cross section, said bridge having a bridge aperture having an aperture shape that complements said non-cylindrical shape to facilitate preventing said bridge from rotating on said locking cross bar.

81. The method as recited in claim 79 wherein said second plate comprises a second plate wall defining a second plate aperture adapted to receive both of said locking cross bar and said second plate aperture, said method further comprising the step of:
situating an end of said locking cross bar into said second plate aperture.

82. The method as recited in claim 81 wherein said second plate comprises a lock associated with said second plate aperture for locking said locking cross bar in said second plate, said method further comprising the step of
actuating said lock so that said bridge and said locking cross bar are locked in said second plate aperture.

83. The method as recited in claim 82 wherein said lock comprises a set screw and said bridge comprising a threaded opening for receiving said set screw and permitting said set screw to engage said locking cross bar, said set screw cooperating with said wall to lock at least a portion of said bridge and said locking cross bar therebetween.

84. The method as recited in claim 78 wherein said method comprises the step of:
providing a locking cross bar and said bridge that are made of different materials.

85. The method as recited in claim 78 wherein method comprises the step of:
selecting said bridge in response to a local anatomy or at least one anatomical or pathological characteristic.

86. The method as recited in claim 85 wherein said method further comprises the step of:
providing a plurality of bridges of different sizes or shapes;
selecting said bridge from said plurality of bridges in response to said at least one anatomical or pathological characteristic.

87. The method as recited in claim 78 wherein said bridge comprises an aperture and a notched-out area in communication with said aperture to allow for mounting of said locking cross bar into said bridge.

88. The method as recited in claim 78 wherein said bridge is generally C-shaped in cross section.

89. The method as recited in claim 78 wherein said locking cross bar comprises an elongated portion having a head, said first plate comprising a first wall defining a first plate aperture for receiving said elongated portion until said head engages said first plate, said second plate having a second plate wall that defines a second plate aperture that is adapted to receive both said bridge and said elongated portion after said bridge is mounted thereon, said second plate comprising a threaded aperture in communication with said second plate aperture for receiving a screw; said method further comprising the step of:

mounting said locking cross bar through said first plate aperture;

positioning said first plate into engagement with said first and second spinous process so that said locking cross bar extends into or through a spinous process aperture defined by said first and second spinous process;

positioning locking cross bar and said bridge through said second plate aperture until said second plate into engages said first and second spinous processes; and screwing a set screw in said threaded aperture and into engagement with at least one of said bridge and said elongated portion to lock said locking cross bar and said bridge in said second plate.

90. The method as recited in claim 89 wherein said of said locking cross bar is integrally formed in said first plate.

91. The method as recited in claim 89 wherein said method further comprises a step of:

slidably mounting said bridge on said locking cross bar.

\* \* \* \* \*